US008110218B2

(12) United States Patent
Balu-Iyer et al.

(10) Patent No.: US 8,110,218 B2
(45) Date of Patent: Feb. 7, 2012

(54) COMPOSITIONS AND METHODS FOR LESS IMMUNOGENIC PROTEIN-LIPID COMPLEXES

(75) Inventors: Sathy V. Balu-Iyer, Amherst, NY (US); Robert Straubinger, Amherst, NY (US); Karthik Ramani, Thiruvamiyur Chennai (IN); Razvan D. Miclea, Simi Valley, CA (US)

(73) Assignee: The Research Foundation of State University of New York, Amherst, NY (US)

( * ) Notice: Subject to any disclaimer, the term of this patent is extended or adjusted under 35 U.S.C. 154(b) by 412 days.

(21) Appl. No.: 12/181,178

(22) Filed: Jul. 28, 2008

(65) Prior Publication Data
US 2009/0053297 A1 Feb. 26, 2009

Related U.S. Application Data

(63) Continuation-in-part of application No. 11/477,583, filed on Jun. 29, 2006, now abandoned, and a continuation-in-part of application No. 10/872,638, filed on Jun. 21, 2004, now Pat. No. 7,625,584, which is a continuation-in-part of application No. 10/000,226, filed on Nov. 30, 2001, now abandoned, said application No. 10/872,638 is a continuation-in-part of application No. 09/997,936, filed on Nov. 30, 2001, now abandoned.

(60) Provisional application No. 60/695,080, filed on Jun. 29, 2005, provisional application No. 60/250,283, filed on Nov. 30, 2000, provisional application No. 60/250,137, filed on Nov. 30, 2000.

(51) Int. Cl.
*A61K 9/127* (2006.01)
*A61K 38/37* (2006.01)
(52) U.S. Cl. ........ 424/450; 424/94.3; 435/174; 435/458
(58) Field of Classification Search .................. 424/450, 424/94.3; 435/174, 458; 530/350, 412
See application file for complete search history.

(56) References Cited

U.S. PATENT DOCUMENTS

| 4,127,502 | A | 11/1978 | Li Mutti et al. |
|---|---|---|---|
| 4,196,191 | A | 4/1980 | Almeida et al. |
| 4,795,806 | A | 1/1989 | Brown et al. |
| 4,965,344 | A | 10/1990 | Hermann |
| 5,013,556 | A | 5/1991 | Woodle et al. |
| 5,474,892 | A | 12/1995 | Jakob et al. |
| 5,580,856 | A | 12/1996 | Prestrelski et al. |
| 5,679,582 | A | 10/1997 | Bowie et al. |
| 5,935,810 | A | 8/1999 | Friedman et al. |
| 5,952,198 | A | 9/1999 | Chan |
| 5,981,714 | A | 11/1999 | Cheng et al. |
| 6,187,304 | B1 | 2/2001 | Jin et al. |
| 6,245,359 | B1 | 6/2001 | Milstein et al. |
| 6,348,215 | B1 | 2/2002 | Straubinger et al. |
| 6,447,800 | B2 | 9/2002 | Hope |
| 6,528,325 | B1 | 3/2003 | Hubscher et al. |
| 6,593,294 | B1 | 7/2003 | Baru et al. |
| 7,160,554 | B2 * | 1/2007 | Zalipsky et al. ............... 424/450 |
| 2002/0098192 | A1 | 7/2002 | Whitlow et al. |
| 2002/0127635 | A1 | 9/2002 | Balasubramanian et al. |
| 2002/0132982 | A1 | 9/2002 | Balasubramanian et al. |
| 2003/0118539 | A1 | 6/2003 | Fahl et al. |
| 2003/0176331 | A1 | 9/2003 | Rosenblum et al. |
| 2004/0229793 | A1 | 11/2004 | Balasubramanian et al. |
| 2005/0026242 | A1 | 2/2005 | Balasubramanian et al. |

FOREIGN PATENT DOCUMENTS

| WO | WO9504524 A1 | 2/1995 |
|---|---|---|
| WO | WO9955306 A1 | 11/1999 |
| WO | 0243665 A2 | 6/2002 |
| WO | WO02061036 A2 | 8/2002 |
| WO | 2005017526 A1 | 2/2005 |

OTHER PUBLICATIONS

Kanaoka et al.; Stabilization of aerosolized IFN-y by liposomes; International Journal of Pharmaceutics, 1999, v

OTHER PUBLICATIONS

Niclas, Daniel, et al., Encapsulation and Protection of the Antibacterial Enzyme, Lysozyme, by Unilamellar Lipid Vesicles, Book of Abstracts, 215th ACS National Meeting, Dallas, Mar. 29-Apr. 2, 1998, American Chemical Society, Washington, D.C., United States (abstract only—downloaded from STN Sep. 17, 2008).

Kuboi, Ryochi, et al., Refolding of Carbonic Anhydrase Assisted by 1-Palmitoyl-2-oleoyl-sn-glycero-3-phosphocholine Liposomes, Biotechnol. Prog., 1997, pp. 828-836, 13, American Chemical Society and American Institute of Chemical Engineers.

Papahadjopoulos, D., et al., Sterically Stabilized Liposomes: Improvements in Pharmacokinetics and Antitumor Therapeutic Efficacy, Dec. 1991, pp. 11460-11464, vol. 88, Proc. Natl. Acad. Sci., NY, United States.

Balasubramanian, Sathyamangalam V., et al., Liposomes as Formulation Excipients for Protein Pharmaceuticals: A Model Protein Study, Pharmaceutical Research, 2000, pp. 344-350, vol. 17, No. 3, Plenum Publishing Corporation.

Yoshimoto, Makoto, et al., Oxidative Refolding of Denatured/Reduced Lysozyme Utilizing the Chaperone-like Function of Liposomes and Immobilized Liposome Chromatography, Biotechnol. Prog., 1999, pp. 480-487, vol. 15, American Chemical Society and American Institute of Chemical Engineers.

Edelhoch, Harold, The Denaturation of Pepsin. III The Effects of Various Protein Denaturants on the Kinetics of Pepsin Inactivation, Journal of the American Chem. Society, 1958, pp. 6648-6655, vol. 80.

Parodi, Rosa Maria, et al., Thermodynamics of Unfolding of Lysozyme in Aqueous Alcohol Solutions, The Journal of Biological Chemistry, Jun. 10, 1973, pp. 4047-4051, vol. 248, No. 11, United States.

\* cited by examiner

Table 2
Liposome size, protein association efficiency, and immunogenicity

| | | | | | | Titers ± SD | |
|---|---|---|---|---|---|---|---|
| Protein | Lipid ratio | Lipid composition | | Size (nm) | Assoc efficiency (%) | Total SC | Inhibitors SC |
| rFVIII | | | | | | 13160 ± 7900 (n=15) | 689 ± 306 (n =13 ) |
| rFVIII | 1:10000 | DMPC:BPS | 70:30 | 200 | 47 | 5670 ± 1255 (n =15 ) | 215 ± 71 (n =14 ) |
| rFVIII | 1:10000 | DMPC:BPS: DMPE-PEG2000 | 70:30:3 | 200 | 34 | 1123 ± 656 (n =12 ) | 73 ± 108 (n =12) |
| rFVIII | 1:10000 | DMPC:BPS: DMPE-PEG2000 | 70:30:15 | 200 | 25 | 4231 ±1764 (n =10 ) | 245 ± 226 (n =10 ) |
| rFVIII | 1:10000 | DMPC:BPS | 90:10 | 100 | 23 | | |
| rFVIII | 1:10000 | DMPC:BPS:DOPE | 80:10:10 | 100 | 25 | | |
| rFVIII | 1:10000 | DMPC:BPS:DOPE | 70:10:20 | 100 | 40 | | |
| rFVIII | 1:10000 | DMPC:BPS:DOPE: DMPE- PEG 2000 | 70:10:20:3 | 200 | 34 | 3822 ± 1144 (n=9) | 246 ± 144 (n =9 ) |
| rFVIII | 1:10000 | DMPC:BPS:DOPE: DMPE - PEG 2000 | 70:10:20:3 | 100 | 36 | 2500 ± 1800 (n = 10) | 152 ± 142 (n =10 ) |

Figure 7

COMPOSITIONS AND METHODS FOR LESS IMMUNOGENIC PROTEIN-LIPID COMPLEXES

This application is a continuation-in-part of now abandoned U.S. application Ser. No. 11/477,583 filed on Jun. 29, 2006, which in turn claims priority to U.S. Provisional Application No. 60/695,080 filed on Jun. 29, 2005, and is also a continuation-in-part of U.S. application Ser. No. 10/872,638 filed Jun. 21, 2004, now U.S. Pat. No. 7,625,584 which is a continuation-in-part of U.S. application Ser. No. 10/000,226 filed on Nov. 30, 2001, now abandoned which in turn claims priority of U.S. Provisional Application No. 60/250,283 filed on Nov. 30, 2000, and U.S. application Ser. No. 09/997,936 filed on Nov. 30, 2001, now abandoned which in turn claims priority to U.S. Provisional Application No. 60/250,137 filed Nov. 30, 2000. The disclosures of all of the above applications are incorporated herein by reference.

This work was supported by Government funds under grant No. R01 HL-70227 from the National Institutes of Health. The Government has certain rights in the invention.

FIELD OF THE INVENTION

This invention generally relates to means for reducing immunogenicity of therapeutics and more particularly provides compositions and methods for reducing the immunogenicity of Factor VIII.

BACKGROUND OF THE INVENTION

Hemophilia A is an inherited bleeding disorder characterized by the deficiency or dysfunction of Factor VIII (FVIII). FVIII serves as a critical co-factor in the intrinsic pathway of the coagulation cascade. Replacement therapy with recombinant human FVIII (rFVIII) or plasma-derived FVIII is the most common therapy employed in controlling bleeding episodes. However, the induction of neutralizing antibodies against the administered protein in approximately 15-30% of patients is a major complication in therapy [1-3]. The neutralizing antibodies frequently target the C2 domain, which is also involved in binding to phospholipids in vivo.

FVIII is a large multi-domain glycoprotein consisting of domains A1, A2, B, A3, C1 and C2 [4,5]. Systematic epitope mapping studies have revealed that anti-FVIII antibodies mainly target defined regions in the A2 (heavy chain), A3 and C2 domains (light chain) of FVIII [6,7]. The epitope determinant within the A2 domain has been mapped to residues Arg484-Ile-508 [8,9]. Antibodies targeting this region have been shown to inhibit the activated form of FVIII (FVIIIa) by blocking interaction of A2 domain with factor IXa (FIXa) [10]. The major epitope determinant within the A3 domain comprises residues 1811-1818 and antibodies against this region also prevent interaction of FVIII with FIXa resulting in loss of cofactor activity [11]. The epitope determinants within the C2 domain have been mapped to residues 2181-2312 [12,13] which encompass the immunodominant, universal CD4+ epitopes, 2191-2210, 2241-2290, 2291-2330 [14,15]. Antibodies against the C2 domain interfere with the binding of FVIII to platelet membrane surface, which is rich in phosphatidylserine (PS), that is essential for the amplification of the coagulation cascade.

Because of the immune response, generated against administered Factor VIII, there is a need for identification of formulations in which the immunogenicity of Factor VIII is reduced preferably without adversely affecting the circulating half life.

SUMMARY OF THE INVENTION

We investigated whether use of liposomes and other lipidic structures comprising negatively charged lipids (such as phospholipids including, but not limited to, phosphatidylserine) and polyethylene glycol (PEG)-derivatized phospholipids can alter the immunogenicity of proteins such as Factor VIII.

In one example, immunogenicity of rFVIII associated with and/or incorporated into liposomes comprising PS and PEG-derivatized PE was evaluated in a murine model for hemophilia A. Animals treated with these compositions had lower titers of both total- and inhibitory anti-rFVIII antibodies, compared to animals treated with rFVIII alone. The mean stimulation index of spleen cells isolated from animals receiving compositions of the present invention was lower than for animals that received rFVIII alone. Cytokine analysis suggested that the reduction in immunogenicity of rFVIII administered in the presence of these liposomal compositions may be mediated, in part, by reduced IL-10 production. Pharmacokinetic studies following intravenous (i.v.) dosing indicated that the circulation half-life of rFVIII using these compositions was increased.

Accordingly, provided herein are compositions in which the immunogenicity of the protein is reduced without significantly compromising the circulating half life. The compositions comprise liposomes and/or other lipidic structures comprising negatively charged lipids, amphipathic lipids derivatized with PEG, and a protein such as FVIII. The liposomes or other lipid structures comprising PEG as described herein, are referred to in this application as being "PEGylated". Also provided are methods for the preparation and use of the compositions.

The abbreviations used herein are: APTT, activated partial thromboplastin time; ACD, acid citrate dextrose; BPS, brain phosphatidylserine; BSA, bovine serum albumin; DMPC, dimyristoylphosphatidylcholine; DMPE-PEG$_{2000}$, 1,2-dimyristoyl-sn-glycero-3-phosphoethanolamine-N-[methoxy(polyethylene glycol)-2000]; ELISA, enzyme-linked immunosorbent assay; FVIIIa, activated FVIII; FIXa, Factor IXa; Ig, immunoglobulin; KO, knockout; PB, phosphate buffer; PBA, phosphate buffer containing albumin; PBT, phosphate buffer containing Tween; PA, phosphatidic acid; PC; phosphatidylglycerol, PG; phosphatidylcholine; PS, phosphatidylserine; rFVIIa, recombinant FVIIIa; rFVIII, recombinant human factor VIII; RES, reticuloendothelial system; TB, Tris buffer.

BRIEF DESCRIPTION OF THE DRAWINGS

FIG. 7: Examples of some liposomal compositions of the present invention and their liposome size, protein association efficiency, and immunogenicity.

DESCRIPTION OF THE INVENTION

Figure 1:
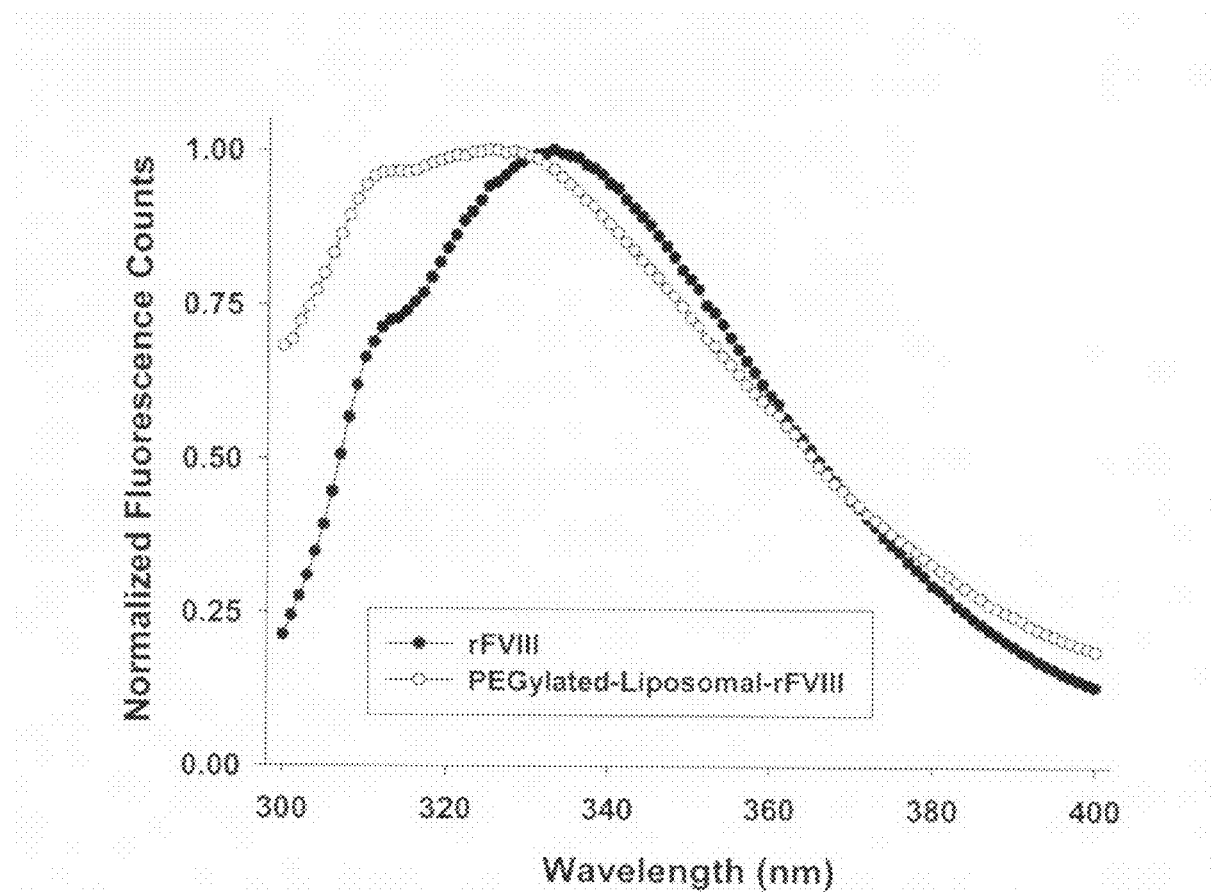
FIG. 1: Tertiary structure of rFVIII in the presence and absence and PEGylated liposomes. Fluorescence emission spectrum was acquired in the range of 300-400 nm. The excitation monochromator was set at 280 nm. The protein concentration used was ~4 µg/ml.

The present invention provides rFVIII formulations. In one embodiment, the formulations comprise liposomes and/or other lipidic structures (such as micelles or cochleates) comprising a negatively charged lipid such as PS or PA. In another embodiment, the liposomes can also comprise a first amphipathic lipid derivatized with PEG (such as PE) and a second amphipathic lipid such as PC, PE (not derivatized with PEG) or PG. In yet another embodiment, in addition to the negatively charged lipid, the micelles comprise PC and/or non-PEG derivatized PE. In still another embodiment, in addition to the negatively charged lipid, the cochleates can also comprise PC.

The compositions of the present invention are such that FVIII is less immunogenic and has longer circulating half life than free FVIII. In particular, this invention provides lipidic-rFVIII preparations in which the immunodominant epitopes are shielded. Because of low immunogenicity and longer circulating half life, the frequency of administration of the protein can be reduced.

The term "derivatized" as used herein means formulation of a covalent bond between a compound and a reagent. Consequently, lipid derivatized PEG or a lipid derivatized with PEG means formation of a covalent bond between a lipid and a PEG molecule.

In general, the compositions of the present invention comprise lipidic structures comprising a negatively charged lipid a PEG derivatized amphipathic lipid. Factor VIII or other proteins or polypeptides can associated with (i.e., surface adsorbed) or be incorporated into these structures. Without intending to be bound by any particular theory, it is considered that the proteins associate with the negatively charged lipids such as PS or PA.

Examples of amphipathic lipids are PC, PE and PG. Examples of negatively charged lipid are PS and PA. An example of a lipid that can be derivatized with PEG is PE. It should be noted that PE can be used in the lipidic structures by itself and/or as derivatized with PEG.

The protein or some part of the protein may be associated with the surface of the lipidic structure or encapsulated by the lipidic structure (as in the case of liposomes and micelles).

In one embodiment, the protein is FVIII. In vivo data is presented in a murine model of hemophilia A. The data indicate that administration of PS containing PEGylated liposomal-rFVIII reduces the immunogenicity of the protein and result in increase in the $t_{1/2}$ of rFVIII.

For the liposomes of the present invention, the amount of the negatively charged lipids is in the range of 30 to 50 mole %. The amount of amphipathic lipids is in the range of 50 to 70 mole %. PE derivatized with PEG is between 1-15 mole %. Optionally, the liposomes may also comprise cholesterol in the range of 0-30 mole %. In one embodiment, the ratio of PC to PS is in the range of 50:50 to 90:10. In one embodiment, the ratio is 70:30. Up to 20% of the PS or PC can be replaced by non-PEG derivatized PE.

The phospholipids of the present invention have two acyl chains. The length of the acyl chains attached to the glycerol backbone varies in length from 12 to 22 carbon atoms. The two acyl chains attached to the glycerol backbone may be the same or different. The acyl chains may be saturated or unsaturated. Some non-limiting examples of 12-22 carbon atom saturated and unsaturated acyl chains are shown in Tables 1A and 1B:

TABLE 1

| Symbol | Common Name | Systematic name | Structure |
|---|---|---|---|
| 12:0 | Lauric acid | dodecanoic acid | $CH_3(CH_2)_{10}COOH$ |
| 14:0 | Myristic acid | tetradecanoic acid | $CH_3(CH_2)_{12}COOH$ |
| 16:0 | Palmitic acid | hexadecanoic acid | $CH_3(CH_2)_{14}COOH$ |
| 18:0 | Stearic acid | octadecanoic acid | $CH_3(CH_2)_{16}COOH$ |
| 20:0 | Arachidic acid | eicosanoic acid | $CH_3(CH_2)_{18}COOH$ |
| 22:0 | Behenic acid | docosanoic acid | $CH_3(CH_2)_{20}COOH$ |

TABLE 1B

| Symbol | Common Name | Systematic name | Structure |
|---|---|---|---|
| 18:1 | Oleic acid | 9-Octadecenoic acid | $CH_3(CH_2)_7CH{=}CH(CH_2)_7COOH$ |
| 16:1 | Palmitoleic acid | 9-Hexadecenoic acid | $CH_3(CH_2)_5CH{=}CH(CH_2)_7COOH$ |

TABLE 1B-continued

| Symbol | Common Name | Systematic name | Structure |
|---|---|---|---|
| 18:2 | Linoleic acid | 9,12-Octadecadienoic acid | $CH_3(CH_2)_4(CH=CHCH_2)_2(CH_2)_6COOH$ |
| 20:4 | Arachidonic acid | 5,8,11,14-Eicosatetraenoic acid | $CH_3(CH_2)_4(CH=CHCH_2)_4(CH_2)_2COOH$ |

Short chain (6-12 carbon atoms) phosphatidylserines are unique water soluble lipids which can exist as micelles at concentrations above the critical micellar concentrations. The short chain phosphatidylserines interact with rFVIII and influence the stability, immunogenicity and pharmacokinetic parameters of rFVIII. PEG derivatized PE can also be used in the micelles.

Additionally, other lipidic structures such as cochleate structures or cylinders comprising negatively charged lipids and PEG derivatized PE can also be prepared. These can be useful as drug delivery systems. For the preparation of cochleates, long chain (12-22 carbon atoms) phospholipids are used.

Micelles may comprise 100 mole % of PS and 1-15 mole % of PEG derivatized PE. Optionally, up to 50% of PS may be replaced by PC and/or up to 5% of PS may be replaced by PE (non derivatized with PEG). For the micelles up to 50% percent of PS may be replaced by PC and/or up to 5% by PE.

Cochleates may also comprise 100 mole % of PS. Up to 30 mole % of the PS may be replaced by PC.

The compositions of the present method can be prepared by several methods. For example in one embodiment, the method comprises preparing liposomes comprising PS, PC and/or PE, associating and/or incorporating (such as by encapsulation) FVIII into the liposomes and adding PEG derivatized PE to the FVIII associated/incorporated liposomes. For the incorporation of PEG derivatized PE into the liposomes, it is preferable to have the PEG derivatized PE at a concentration lower than the critical micelle concentration (CMC) so that preferably micelles are not formed. Generally, the formation of micelles will slow the process of incorporation of PEG derivatized PE into the liposomes.

In another embodiment, PC (and optionally PE), PS and PEG derivatized PE are used to prepared liposomes and then FVIII is added so as to associated with and/or incorporate it into the liposomes.

In another embodiment, incorporation of varying amounts of PEG can be achieved by including varying amounts of activated PE (activated via amino, carboxyl or thiol groups) and after the incorporation of FVIII the activated PE can be covalently linked to the PEG. Presence of PE has been shown to improve the binding properties of FVIII with PS. In a variation of this embodiment, a spacer can be used between the PE and PEG. A suitable spacer has between 6-12 carbon atoms. Other spacers having the same length as 6-12 carbon atoms can be used.

In a further embodiment, the liposomes of the lipid structures may also comprise cholesterol. For this embodiment, cholesterol is added in the step of making the liposomes or the other lipid structures.

The liposomes of the present invention are between 80 to 500 nm. In one embodiment, the liposomes are 100 to 200 nm in diameter. The molar ratio of protein to lipid is between 1:1000 to 1:20,000. The cochleates are generally formed in buffers with high viscosity and have a mean range varying between 150 to 300 nm. Micelles are in the range of 70 to 90 nm.

The polyethylene glycol useful in the present invention can have molecular weights between 700 to 30,000. Examples of useful molecular weights for PEG included, but are not limited to, 750, 1000, 2000, 3000, 5000, 20000, 30000 Daltons (Da). A variety of methods are known for derivatizing PEG to a lipid, i.e. incorporating a PEG molecule into a lipid. For example, the derivatization can be done through a cyanuric chloride group or by using a carbonyl diimidazole coupling reagent. More details can be found in U.S. Pat. No. 5,013,556, which method of derivitization is incorporated herein by reference. A variety of PEG derivatized PE lipids are commercially available. Examples include, but are not limited to, dimyristoyl-phosphoethanolamine-PEG (DMPE-PEG); dipalmitoyl phosphatidylethanolamine-PEG (DPPE-PEG); and distearoyl phosphatidylethanolamine-PEG (DSPE-PEG). As an example, the derivatization of PE with PEG is through covalent bonding.

Examples of useful liposomal compositions and their properties are presented in Table 3 (FIG. 7).

The following examples are presented to illustrate the present invention. They are not intended to be limiting in any manner.

Example 1

This example describes the preparation of PC containing liposomes. In this example, the protein was first associated with PS containing liposomes and then PEG was added.

Materials rFVIII (Baxter Biosciences, Carlsbad, Calif.) was used as the antigen. Normal coagulation control plasma and FVIII deficient plasma for the activity assay was purchased from Trinity Biotech (Co Wicklow, Ireland). Brain phosphatidylserine (BPS), dimyristoyl phosphatidylcholine (DMPC) and 1,2-dimyristoyl-sn-glycero-3-phosphoethanolamine-N-[methoxy(polyethylene glycol)-2000] (DMPE-PEG$_{2000}$) dissolved in chloroform were obtained from Avanti Polar Lipids (Alabaster, Ala.), stored at −70° C. and used without further purification. Sterile, pyrogen-free water was purchased from Henry Schein Inc. (Melville, N.Y.). Goat anti-mouse immunoglobulin (Ig, IgM+IgG+IgA, H+L) conjugated to alkaline phosphatase was from Southern Biotechnology Associates, Inc. (Birmingham, Ala.). Monoclonal antibody ESH 8 was obtained from American Diagnostica Inc, (Greenwich, Conn.). IgG free bovine serum albumin (BSA), diethanolamine and acetone was obtained from Sigma (Saint Louis, Mo.). p-Nitrophenyl phosphate disodium salt was purchased from Pierce (Rockford, Ill.). 1,6-diphenyl-1,3,5-hexatriene (DPH), RPMI-1640 culture medium, penicillin, streptomycin, L-Glutamine, 2-mercaptoethanol and Polymyxin B were all obtained from Invitrogen Corp., (Carlsbad, Calif.). $^3$H-thymidine was obtained from Perkin Elmer Inc. (Boston, Mass.). All other buffer salts used in the study were obtained from Fisher Scientific (Fairlawn, N.J.) and were used without purification.

Determination of Critical Micellar Concentration (CMC) of DMPE-PEG$_{2000}$:

CMC of DMPE-PEG$_{2000}$ was determined using the fluorescence probe diphenylhexatriene (DPH) as described previously [16]. Briefly, DPH solution (2 µl, [DPH]=30 µM in acetone) was added to various concentrations of 1 ml DMPE-PEG$_{2000}$ followed by incubation at 37° C. for 2 h. The fluorescence intensity of the dispersions was measured using a fluorometer (Photon Technology International, Lawrenceville, N.J.) equipped with a xenon arc lamp. The excitation wavelength (Ex) of the probe was set at 360 nm and emission (Em) was monitored at 430 nm. The concentration of the dispersion where the fluorescence intensity increased abruptly was defined as the CMC and was found to be ~100 µM.

Preparation of Polyethylene Glycol-(PEGylated) PS Liposomes:

PEG Transfer Methodology

Required amounts of DMPC ($T_c$~23° C.) and BPS ($T_c$~6-8° C. were dissolved in chloroform and the solvent was evaporated using a rotary evaporator (Buchi-R200, Fisher Scientific) to form a thin film on the walls of a round-bottomed flask. Any residual solvent was removed from the sample under a stream of dry nitrogen. Liposomes were formed by rehydrating the thin lipid film in Tris buffer (TB, 300 mM NaCl, 25 mM Tris, 5 mM CaCl$_2$.2H$_2$O, pH=7.0, prepared in sterile pyrogen free water) at 37°. The molar ratios of the lipids used in the present study were DMPC:BPS (70:30 mol %). The liposomes were extruded through triple-stacked 200 nm polycarbonate membrane several times using a high-pressure extruder (Mico, Inc., Middleton, Wis.) at a pressure of ~200-250 psi. Liposomes were sterile filtered through a 0.22 µm Millex™-GP filter unit (Millipore Corporation, Bedford, Mass.). Lipid recovery was estimated by determination of phosphorous content by the method of Bartlett [17]. The size distribution of the liposomes was determined using a particle size analyzer (Nicomp Model CW 380, Particle Sizing Systems, Santa Barbara, Calif.) as described previously [18]. The sized liposomes were associated with appropriate amount of rFVIII by incubating at 37° C. with gentle swirling for 30 minutes. PEGylation of the protein-liposome mixture was achieved by the addition of the protein-liposome mixture to a dry film of DMPE-PEG$_{2000}$. It was ensured that the volume of protein-liposome mixture added to the dry PEG film did not result in the formation of PEG micelles. Incorporation of PEG was confirmed by matrix-assisted laser desorption/ionization time-of-flight (MALDI-TOF) mass spectrometry (data not shown). The final mol % of PEG in the preparation was 4 mol % of the total-lipid. The molar ratio between the protein and lipid was maintained at 1:10,000 for all the experiments. To estimate the amount of protein associated with PEGylated liposomes, free protein was separated from PEGylated liposome associated protein using discontinuous dextran density gradient centrifugation technique [19]. The percent of active protein associated was determined by the one-stage APTT assay [20]. The percent association was estimated to be ~27.6±9.6% (±S.E.M, n=5). Preparations were used immediately after preparation.

Theoretical Considerations for the Incorporation of Polyethylene Glycol (PEG) in Liposomes:

In this example, PEG was incorporated into the liposomes following association of the protein on to the surface of the liposomes rather than incorporating the PEG during the preparation of the lipid film. It is considered that this method of PEG incorporation will reduce the possibility of PEG interfering with the ability of the protein to associate with liposomes as a result of steric hindrance. We believe that the following theoretical considerations argue against the possibility that presence of protein on the surface of liposomes compromises the efficiency of insertion of PEG.

The mean diameter of the liposomes used in the study was 200 nm. Under the assumption that the bilayer thickness is 40 Å and the area occupied by each phospholipid molecule is 70 Å$^2$, the number of vesicles/µmol of phospholipid was estimated to be ~1.8×10$^{12}$ vesicles. For immunization studies, 2 µg of protein was administered per animal and based on the molar excess of protein to lipid used (1:10,000), each animal received ~71.4 moles of lipid. Three-dimensional structure of membrane bound FVIII derived by electron crystallography revealed that FVIII domains have a compact arrangement in which the C2 domain of the protein interacts with the phospholipids [21]. Based on the unit cell dimension for the two-dimensional map and the total surface area of the liposomes of 200 mm mean diameter, we estimated that the maximum number of FVIII molecules that could be packed on the surface of the liposomes is ~2400. However, given that the maximum number of protein molecules/vesicle was projected to be ~33 based on the protein to lipid ratio employed in our studies, the above theoretical assessment reveal that the majority of the surface of the liposomes is still unoccupied and available for coating by PEG.

Example 2

These example describes the characteristics of the liposomes prepared in Example 1.

Fluorescence Spectroscopy

Emission spectra of rFVIII and rFVIII associated with PEGylated liposomes were obtained using a fluorometer (Quanta Master, Photon Technology International, Lawrenceville, N.J.). The samples were excited at 280 nm and the emission spectrum was obtained from 300-400 nm. A slit width of 4 nm was used on both the excitation and emission paths. The protein concentration was ~4 µg/ml and a variable pathlength cuvette was used to minimize inner filter effects.

Tertiary structural changes in the protein were investigated by fluorescence spectroscopy (FIG. 1). The emission spectrum of free FVIII showed an emission maximum of 333 nm. The protein associated with PEGylated liposomes displayed a significant blue shift in the emission maxima to 325 nm and was accompanied by a large increase in intensity (data not shown). The pronounced blue shift in emission maximum suggests the possibility of substantial intercalation or encapsulation of hydrophobic domains of rFVIII into the liposome bilayer. This was in contrast to the modest changes in the emission spectrum that was observed following association of the protein to liposomes lacking PEG. In the absence of PEG, the data indicated only minimal conformational changes and the majority of the protein in the membrane bound form was on the surface of the liposomes. Without intending to be bound by any particular theory, it is considered that the wavelength shift is the result of change in the dielectric constant in the microenvironment of tryptophan (Trp) residues that participate in membrane binding due to presence of PEG on the surface of liposomes or reduced accessibility of solvent molecules to the Trp residues due to steric effect of PEG. Changes in the dielectric constant of the surrounding solvent has been shown to influence the stoke shift of a fluorophore by altering the organization of the solvent molecules around the excited state of the fluorophore [25].

Example 3

This example describes the preparation of PS containing micelles. Lipid films comprised of dicaproyl phosphatidylserine (DCPS) and dicaproyl phosphatidylthioethanol (DCPSE) (97:3 molar ratio, total lipid 5 μmoles) were prepared from a chloroform stock solution by evaporating the solvent in a rotary evaporator. The films were reconstituted with 1 mL Tris buffer (5 mM $CaCl_2$, 25 mM Tris and 300 mM NaCl, pH=7) by vortex mixing to obtain 5 mM lipid solutions. Concentrated rFVIII stock was diluted with the 5 mM lipid solution and incubated at 37° C. for 30 minutes. The PEGylation approach is similar to the PEGylation of the preformed liposomes using activated PEG molecules. PEGylation was achieved by coupling an activated PEG molecule (linear or branched mPEG maleimide) to the free thiol group present on the phospholipid headgroup (DCPSE).

Example 4

This example describes the preparation of PS containing cochleate structures or cylinders. Sized liposomes of 100 nm or less containing pure brain phosphatidylserine (BPS) and dioleoyl phosphatidylthioethanolamine (DOPSE) (molar ratio 99:1) were prepared in a $Ca^{2+}$-free Tris buffer. rFVIII-liposome complex was generated by incubating concentrated rFVIII solutions in the presence of the sized liposomes for 30 minutes at 37° C. The viscosity of the rFVIII liposomal complex was increased by adding dextran solution (20% w/v) to achieve a final dextran concentration of 5 or 10% w/v. The controlled growth of cochleates cylinders is initiated by spiking Ca ions in the solution (final concentration 5 mM) and incubating the mixture at lower temperature for 30 minutes. PEGylation was achieved by coupling an activated PEG molecule (linear or branched mPEG maleimide) to the free thiol group present on the phospholipid headgroup (DOPSE)). In addition, PEGylation of nanocochleate cylinders can be carried out by engineering a covalent bond between activated PEG molecules (N-hydroxysuccinimide ester of PEG carboxylic acids (PEG-NHS)) and free amino group present on BPS head group. Direct PEGylation of rFVIII by the PEG-NHS reagent is very unlikely based on a large excess of amino groups present on the PS headgroup.

Example 5

This example describes the complexation of rFVIII liposomal complex with PEG by activated PEG technology. DMPC:BPS:dioleoyl phosphatidylthioethanol (DOPSE) liposomes (molar ratio 70:25:5) were prepared as described below. The required amounts of DMPC, BPS and DOPSE were dissolved in chloroform. A thin lipid film was formed on the walls of a glass tube, by removing the solvent in a rotary evaporator (Buchi-R200, Fisher Scientific). The liposomes were prepared by rehydration of the lipid film with Tris buffer (TB 25 mm Tris, 300 mM NaCl, 5 mM $CaCl_2$ pH=7.4) at 37° C. The liposomes were extruded eight times through double stacked 100 nm polycarbonate membranes using a high pressure extruder (Lipex Biomembranes, Inc.) at a pressure of ~200 psi. The size distribution of the particles was monitored using a particle size analyzer (aNicomp model CW380, Particle Sizing System).

Liposomal Protein Preparation

The association of the protein with the preformed liposomes was achieved by incubating the protein in the presence of the liposomes at 37° C. for 30 minutes with occasional gentle swirling. The protein to molar ratio was maintained the same for all preparations (1:10,000).

PEGylation can be achieved by engineering a covalent bond between a free thiol group present on the head group of the DOPSE lipid and an activated PEG derivative. Such a derivative can be represented by mPEG-maleimide or branched PEG maleimide. Other activated PEG derivatives that target a free thiol group are equally suitable to form a covalent bond between the liposome and the PEG moiety.

The advantage of this method is that the thiol groups are less frequently present on the surface of protein molecules. Thus the large excess of lipids (protein:lipid ratio is 1:10000 where 5% of lipids are DOPSE) is expected to reduce the binding of activated PEG to rFVIII and diminish its activity.

Example 6

This example describes in vivo studies using the compositions described in Example 1. A colony of hemophilic mice (with a target deletion in exon 16 of the FVIII gene) [22]. Equal numbers of adult male and female mice, aged 8-12 weeks were used for the studies as the characteristics of their immune response to rFVIII have been shown to be comparable [23].

Blood samples were obtained by cardiac puncture and added at a 10:1 (v/v) ratio to acid citrate dextrose (ACD, containing 85 mM sodium citrate, 110 mM D-glucose and 71 mM citric acid). Plasma was separated by centrifugation and samples were stored at −80° C. until analysis. All studies were performed in accordance with the guidelines of Institutional Animal Care and Use Committee (IACUC) at the University at Buffalo.

Immunization of the FVIII knockout mice (n=12) consisted of four subcutaneous (s.c.) injections of rFVIII or rFVIII-PEGylated liposomes (2 μg) at weekly intervals. Blood samples were obtained at the end of 6 weeks.

Antibody Measurements

Detection of Total Anti-rFVIII Antibodies

Total anti-rFVIII antibody titers were determined by ELISA. Briefly, Nunc-Maxisorb 96 well plates were coated with 50 μl of 2.5 μg/ml of rFVIII in carbonate buffer (0.2M, pH=9.4) and incubated at 4° C. overnight. The plates were then washed 6 times with 100 μl of phosphate buffer (PB; 10 mM $Na_2HPO_4$, 1.8 mM $KH_2PO_4$, 14 mM NaCl, 2.7 mM KCl) containing 0.05% Tween 20 (PBT). Nonspecific protein binding sites on the well plate plastic adsorptive surface were blocked by incubating 200 μl of PB buffer containing 1% bovine serum albumin (PBA) for 2 hours at room temperature. The plates were washed 6 times with PBT and then 50 μl of various dilutions of mouse plasma samples in PBA were added and incubated at 37° C. for 1 hour. The plates were washed 6 times with PBT and incubated with 50 μl of 1:1000 dilution of alkaline phosphatase conjugated goat anti-mouse Ig in PBA, at room temperature for 1 hour. The plates were washed 6 times with PBT and 100 μl of 1 mg/ml p-nitrophenyl phosphate solution in diethanolamine buffer (consisting of 1 M diethanolamine, 0.5 mM $MgCl_2$). The plates were incubated at room temperature for 30 minutes and the reaction was quenched by adding 100 μl of 3 N NaOH. The alkaline phosphatase reaction product was determined by absorbance at 405 nm using a Spectramax plate reader (Molecular Devices Corporation, Sunnyvale, Calif.). The immunogenicity results were expressed as follows: linear regression was performed on the absorbance values obtained with monoclonal murine IgG anti-human FVIII antibody, ESH8 that binds to the C2 domain. Half the difference between the maximum and minimum predicted absorbance was calculated as the plate specific factor (PSF). A linear regression of the plot of absorbance values of various dilutions (1:100 to 1:40,000) versus log of dilution was used to calculate the dilution which gave an optical density equal to the PSF. The dilution so obtained was considered the antibody titer of the sample.

Detection of Inhibitory Anti-rFVIII Antibodies

Inhibitory (neutralizing) anti-rFVIII antibodies were detected using the Nijmegen modification of the Bethesda assay [24]. Residual rFVIII activity was measured using the one stage APTT assay [20]. Each dilution was tested in duplicate. One Bethesda Unit (BU) is the inhibitory activity that produces 50% inhibition of rFVIII activity. The point of 50% inhibition was determined by linear regression of data points falling at least within the range of 20-80% inhibition.

T-Cell Proliferation Studies

Female hemophilic mice, aged 8-12 weeks, were immunized using two subcutaneous (s.c.) injections of rFVIII or PEGylated liposomal-rFVIII (2 µg protein per injection) at weekly intervals. Control mice received no rFVIII. Animals were sacrificed three days after the second injection and the spleen was harvested as a source of T-cells. Spleen cells were depleted of CD8+ cells using magnetic beads coated with a rat anti-mouse monoclonal antibody for the Lyt 2 membrane antigen (Dynal Biotech, Oslo, Norway) expressed on CD8 cells, using the manufacturer's protocol. The remaining cells ($2 \times 10^5$ cells/200 µl) were cultured in a 96 well flat bottom plate with rFVIII (100 ng/well or 1000 ng/well) in complete RPMI-1640 culture medium containing 10,000 U/ml penicillin, 10 mg/ml streptomycin, 2.5 mM sodium pyruvate, 4 mM L-Glutamine, 0.05 mM 2-mercaptoethanol, 2 mg/ml Polymyxin B and 0.5% heat inactivated hemophilic mouse serum. One µCi/well of $^3$H-thymidine (6.7 Ci/mmol) was added after 72 h of culture at 37° C. At the end of 16 h, the cells were harvested using a Micromate Harvester (Packard, Meriden, Conn.) and $^3$H-thymidine incorporation was measured using a TopCount™ microplate scintillation and luminescence counter (Packard Instrument Company, Meriden, Conn.). Treatment groups consisted of 3 replicate animals, and cells from each individual mouse were tested in quadruplicate for antigen-dependent proliferation. The data are reported as a stimulation index (SI), which is the ratio of the average $^3$H-thymidine incorporation in the presence of the antigen to the average incorporation in the absence of the antigen. This approach normalized the data of each experiment and allows for comparison of experiments carried out at different times.

Cytokine Analysis

After 72 h of incubation, the supernatants of antigen-stimulated T-cells were collected and stored at −70° C. until further analysis. The supernatant was analyzed by antibody-capture ELISA (R&D systems, Minneapolis, Minn.). IFN-γ was measured as a representative Thelper 1 (Th1) cytokine and IL-10 was measured as a representative Thelper 2 (Th 2) cytokine.

Pharmacokinetics Studies

Twenty-seven male hemophilic mice (20-26 g, 8-12 weeks old) received 400 IU/kg of rFVIII or PEGylated liposomal-rFVIII as a single i.v. bolus injection via the penile vein. Blood samples (~600 µl) were collected 0.08, 0.5, 1, 2, 4, 8, 16, 24, 36 and 48 h post dose by cardiac puncture (n=2-3 mice/time point) and added to ACD. Plasma was separated and stored at −70° C. until analysis. Plasma samples were analyzed for the activity of the protein by the chromogenic assay (Coamatic FVIII, DiaPharma Group, West Chester, Ohio). The activities calculated at each time point were then utilized to estimate the basic pharmacokinetic parameters by non-compartmental analysis using WinNonlin (Pharsight Corporation, Mountainview, Calif.).

Statistical Analysis

Data was analyzed by ANOVA using Analyst Application of SAS (SAS Institute Inc., Cary, N.C.) or Minitab (Minitab Inc., State College, Pa.). Dunnette's post-hoc multiple comparison test was used to detect significant differences ($p<0.05$).

Results

Figure 2A:
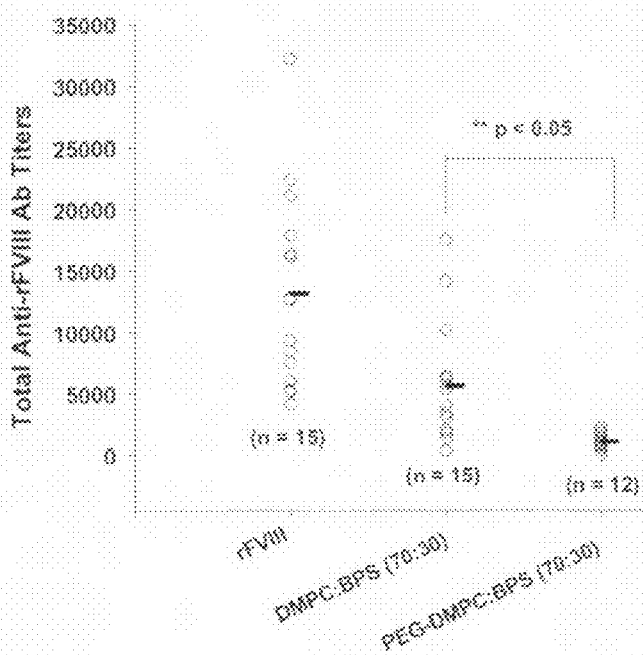
FIGS. 2A and 2B: (A) Total anti-FVIII antibody titers and (B) Inhibitory anti-rFVIII antibodies in hemophilic mice following administration of rFVIII in the absence and presence of PEGylated-liposomes comprising of DMPC:BPS (70:30) at the end of 6 weeks. Each point represents values from individual mouse that received treatment and the horizontal bar depicts the mean of the total antibody or inhibitory titers. For comparison purpose data obtained following administration of rFVIII in the presence of non-PEGylated DMPC: BPS liposome is also displayed. Blood samples were obtained 2 weeks after the 4$^{th}$ injection. The total anti-FVIII antibody titers were determined by ELISA and inhibitory titers were determined by Bethesda Assay. Statistical analysis was carried out as described in the Examples.

Shown in FIG. 2A is the total anti-rFVIII antibody titers in the absence and presence of PEGylated liposomes comprised of DMPC and BPS. Animals treated with PEGylated liposomal-rFVIII displayed significantly lower antibody titer (1123.1±189.5, ±S.E.M, n=12, p-value <0.05) in comparison to animals treated with rFVIII (13,166.7±2042.2, ±S.E.M, n=15). These results indicate that antibody formation is reduced in the presence of PEGylated liposomes.

Figure 2B:
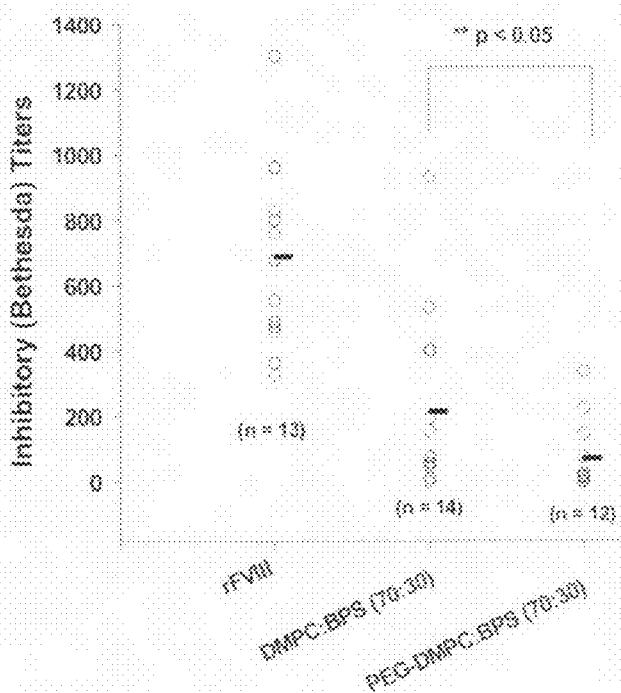

Neutralizing antibodies (i.e., antibodies specific against Factor VIII), which interfere with the activity of the protein, were detected using the Bethesda assay. FIG. 2B shows the inhibitory antibody titers, expressed in Bethesda Units (BU) following rFVIII and PEGylated liposomal-rFVIII treatments at the end of 6 weeks. The data indicated that the neutralizing antibodies were significantly lower in the presence of PEGylated liposomes (73.65±31.25 BU/ml, ±S.E.M, n=12, p-value <0.05) in comparison to rFVIII alone (689.7±78.1 BU/ml, ±S.E.M., n=13). These results indicated that PEGylated liposomes not only reduced the overall anti-FVIII antibody titers but also lowered the titers of antibodies that inactivate the protein. For comparison purpose the total antibody and inhibitory titers following administration of non-PEGylated PC/PS liposomes are also displayed. The data indicated that the mean total antibody and inhibitory titers in the presence of PEGylated liposomes were lower than that of non-PEGylated liposomes, though the differences were not statistically different ($p>0.05$).

Figure 3A:
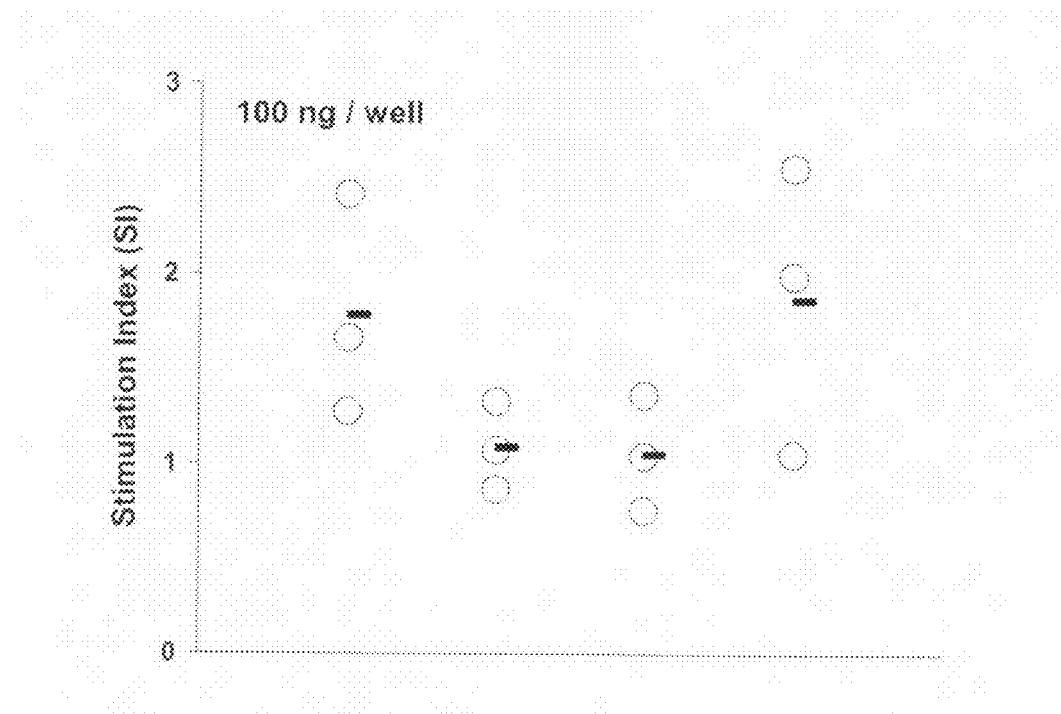
FIGS. 3A and 3B: CD4+ T-cell proliferation response of hemophilic mice, represented as the stimulation index, to intact rFVIII (100 (3A) or 1000 ng/well (3B)) carrying multiple immunodominant epitopes, following two subcutaneous doses of 2 μg rFVIII, non-PEGylated liposomal-rFVIII, PEGylated liposomal-rFVIII or PS free liposomal-rFVIII. Calculation of the stimulation index and the statistical analysis is described in the Examples. Each point represents values from individual animals and the horizontal bar depicts the mean of the stimulation index.
Figure 3B:
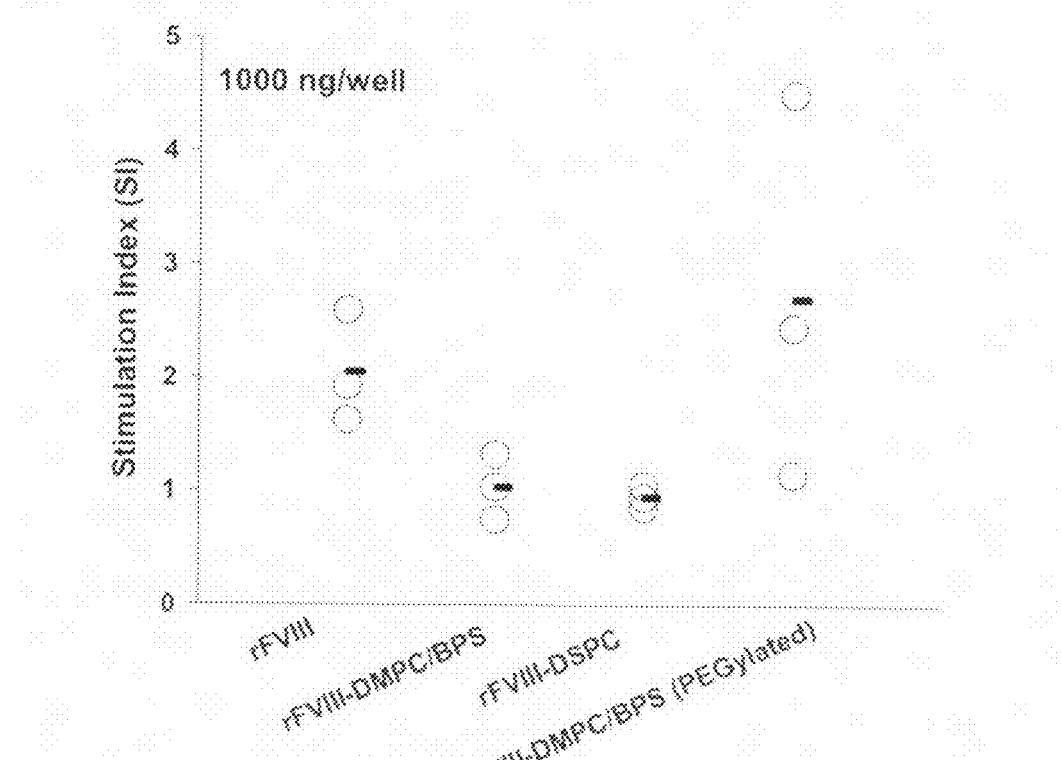

To determine whether FVIII specific T-cells were stimulated in vivo following immunization with PEGylated liposomal-rFVIII, the T-cell proliferation response to rFVIII challenge in vitro was evaluated. The mean stimulation index of spleen cells isolated from animals that received PEGylated liposomal-rFVIII treatment was lower compared to animals that received rFVIII treatment alone (FIGS. 3A & 3B). The data suggest possible differences in the T-cell clones that were activated for clonal expansion depending upon whether animals were exposed to rFVIII in the presence and absence of PEGylated PS-containing liposomes.

Figure 4:
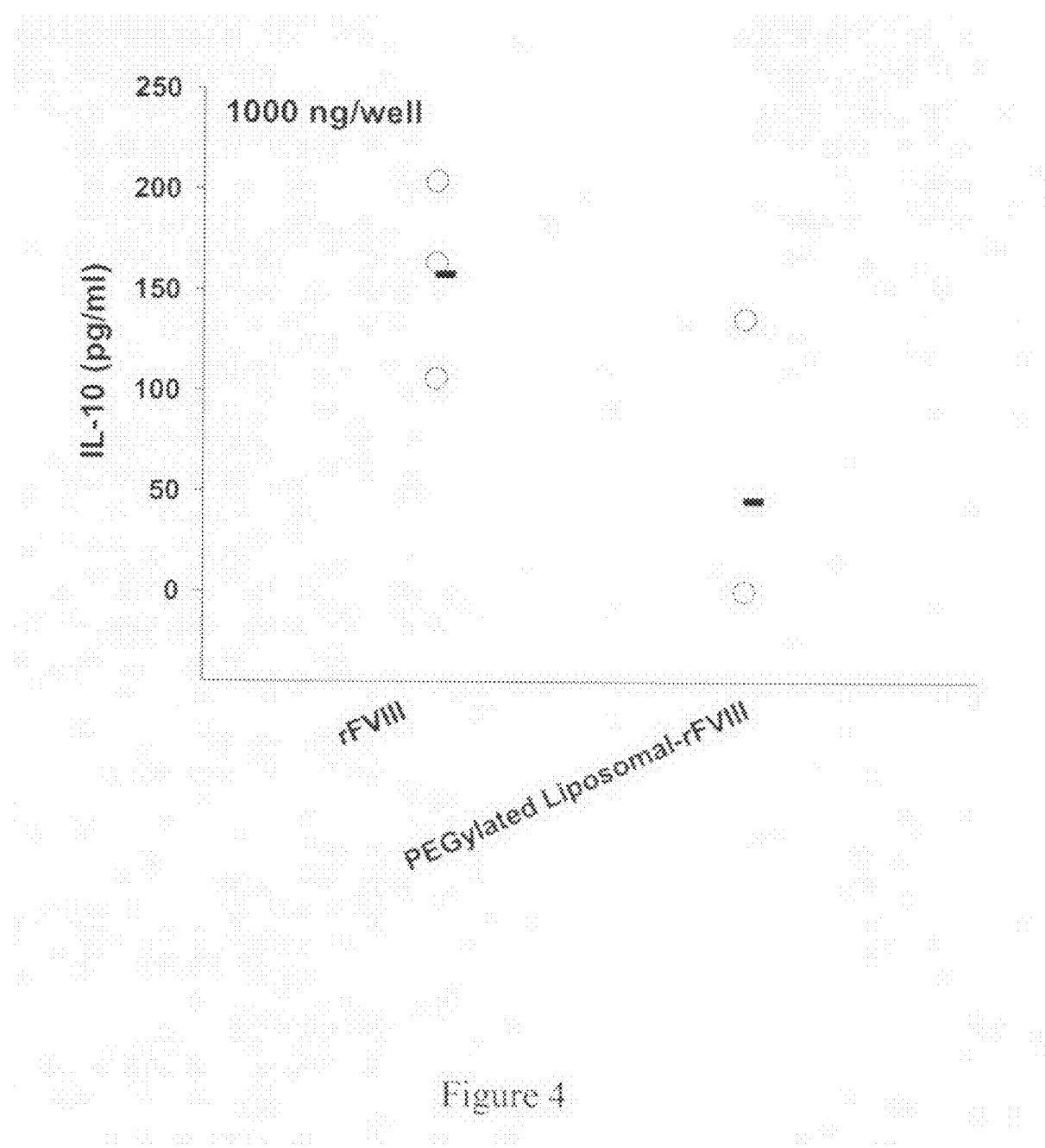
FIG. 4: IL-10 secretion by antigen-challenged CD4+ T-cells from animals administered two subcutaneous doses of 2 μg free rFVIII or PEGylated liposomal-rFVIII. CD4+ enriched T-cells were challenged with rFVIII (1000 ng/well). Each point represents values from individual animals, and the horizontal bar depicts the mean IL-10 level secreted in the culture medium. Statistical analysis was carried out as described in the Examples.

To determine whether the reduction in immunogenicity of rFVIII in the presence of PEGylated PS containing liposomes was a result of reduced IL-10 secretion, cytokine analysis of antigen-stimulated T-cells was carried out following immunization of animals with free- or liposomal-rFVIII. As shown in FIG. 4, the mean IL-10 level secreted by T-cells of animals given rFVIII associated with PEGylated liposomes was lower than for those animals given rFVIII alone. Negligible levels of IFN-γ were detected in the culture medium for all the treatment groups (data not shown). Overall, the data suggest that the reduction in immunogenicity of rFVIII administered in the presence of PEGylated PS-containing liposomes may be mediated, in part, by reduced IL-10 production. Furthermore, the data suggest that the reduction in immunogenicity is not the result of polarization of the Th1/Th2 response.

While not intending to be bound by any particular theory, it is believed that the inclusion of PS in liposomes contributes immunomodulation. Considering that the antibody response to rFVIII is a T-cell dependent process, it is possible that the reduction in immunogenicity of rFVIII in the presence of PEGylated PS containing liposomes may result from repression of rFVIII specific T-cell clones in vivo.

Figure 5:
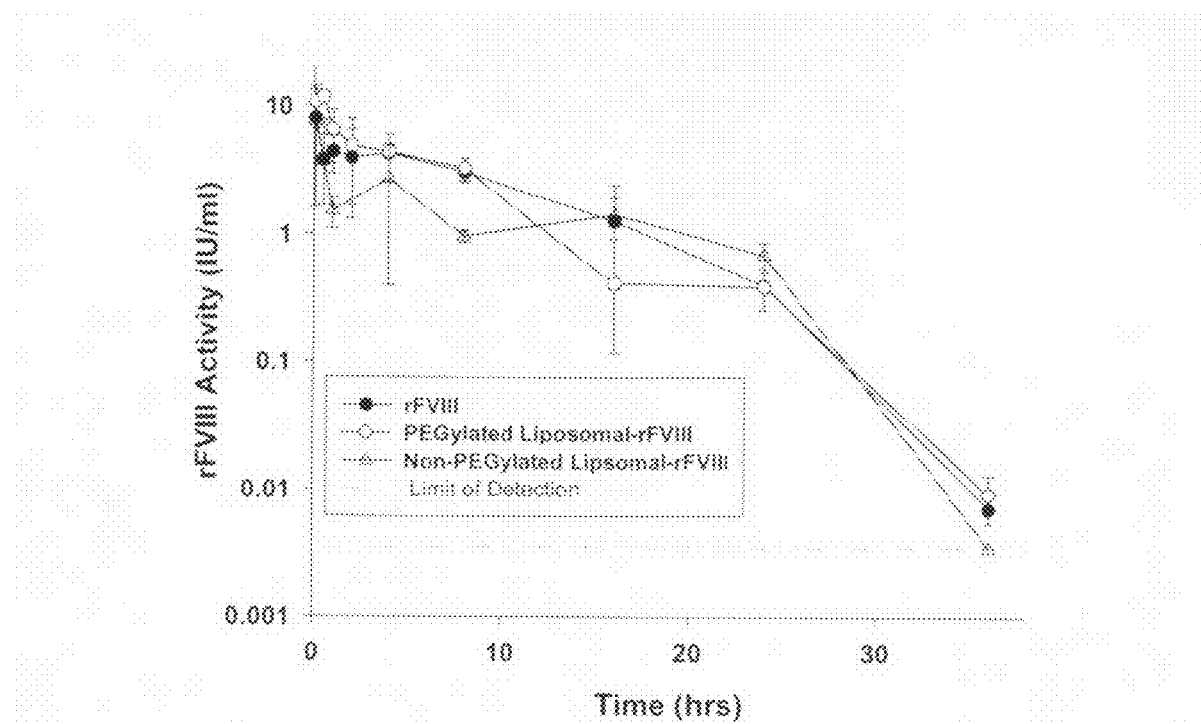
FIG. 5: Plasma rFVIII activity versus time profiles following administration of rFVIII, PEGylated or non-PEGylated liposomal-rFVIII in hemophilic mice.

In addition to the reduction in the immunogenicity of rFVIII, association of rFVIII with PS containing liposomes may also extend the circulation time of rFVIII in vivo and thus reduce the frequency of administration of the protein required to control hemophilia A. Pharmacokinetic (PK) studies suggested that the circulation-half life ($t_{1/2}$) of PEGylated liposomal-rFVIII increased by 35% relative to rFVIII alone (Table 1). The systemic exposure between the treatments was similar (FIG. 5 and Table 2).

TABLE 2

Summary of PK parameters obtained following non-compartmental analysis

|  | Protein:Lipid | Liposomes |  | AUC (IU*hr/mL) | $V_{ss}$ (mL) | CL (mL/hr) | $t_{1/2}$ (hr) |
|---|---|---|---|---|---|---|---|
| rFVIII | — | — |  | ~57 | 1.37 | .17 | 2.6 |
| rFVIII | 1:10,000 | DMPC:BPS * | 70:30 | ~40 | 2.69 | .25 | 1.6 |
| rFVIII | 1:10,000 | DMPC:BPS: DMPE-PEG | 70:30:3 | ~59-72 | 1.03 | .16 | 3.5 |

* At 36 hours post administration, all animals treated with non-PEGylated rFVIII complex, had rFVIII plasma levels bellow the limit of detection. For PK parameter estimation, the plasma levels of rFVIII at 36 hours was set equal to the detection limit (0.035 IU/mL). AUC indicates area under the curve; Vss is volume of distribution at steady state, and CL is clearance.

Example 6

Figure 6:
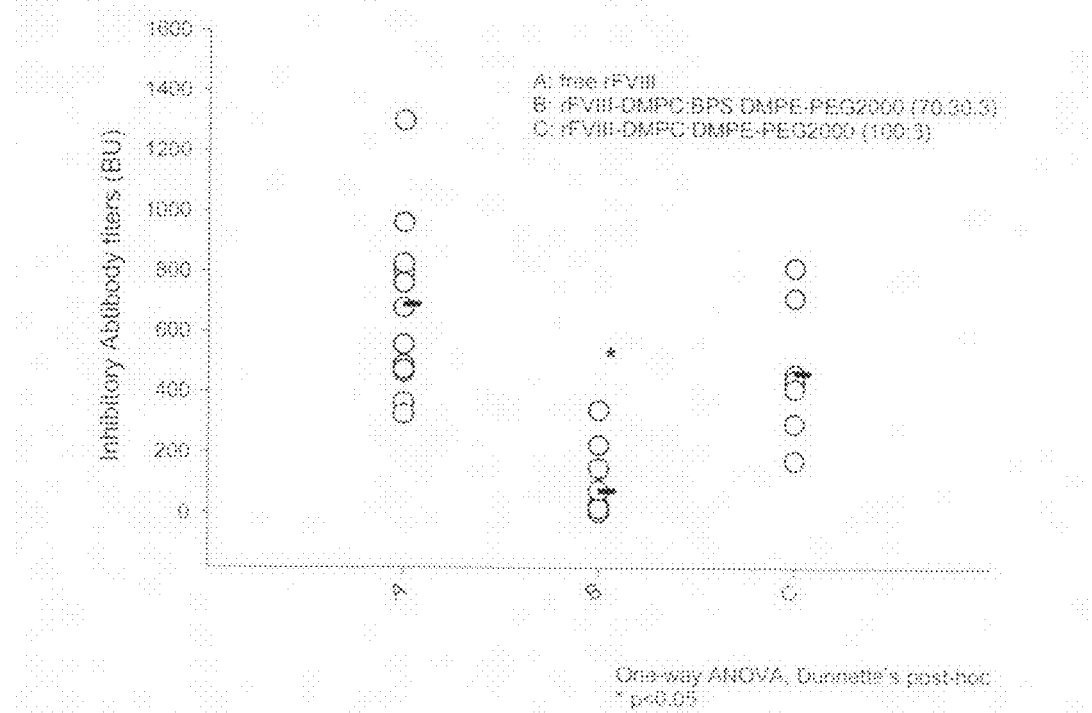
FIG. 6: Inhibitory anti-rFVIII antibodies in hemophilic mice following administration of rFVIII in the absence and presence of PEGylated-liposomes of various lipid compositions at the end of 6 weeks. Each point represents values from individual mouse that received treatment and the horizontal bar depicts the mean of the total antibody or inhibitory titers. Blood samples were obtained 2 weeks after the 4$^{th}$ injection. The inhibitory titers were determined by Bethesda Assay. Statistical analysis was carried out as described in the Examples.

This examples provides a comparative analysis of PEG associated liposomes prepared with or without a negatively charged phospholipids. Inhibitory titers were determined as described in Example 5 for free rFVIII, FVIII associated with or incorporated into liposomes prepared with PS and rFVIII associated with or incorporated into liposomes prepared without PS. As shown in FIG. 6, the inhibitory antibody titers for rFVIII associated with or incorporated into liposomes prepared with PS are significantly lower than the titers for free rFVIII and for rFVIII associated with or incorporated into liposomes prepared without PS.

Those skilled in the art can optimize individual preparations. In addition, the observation that the immunogenicity of PS containing PEGylated liposomal-rFVIII is much lower than rFVIII alone represents a significant progress towards the development of formulations that are less immunogenic.

REFERENCES

[1] J. Klinge, N. M. Ananyeva, C. A. Hauser, E. L. Saenko, Hemophilia A—from basic science to clinical practice, Semin Thromb Hemost 28 (2002) 309-322.
[2] K. Fijnvandraat, W. S. Bril, J. Voorberg, Immunobiology of inhibitor development in hemophilia A, Semin Thromb Hemost 29 (2003) 61-68.
[3] P. Lollar, Molecular characterization of the immune response to factor VIII, Vox Sang 83 Suppl 1 (2002) 403-408.
[4] P. A. Foster, T. S. Zimmerman, Factor VIII structure and function, Blood Rev 3 (1989) 180-191.
[5] P. J. Fay, Factor VIII structure and function, Thromb Haemost 70 (1993) 63-67.
[6] D. Scandella, M. Mattingly, S. de Graaf, C. A. Fulcher, Localization of epitopes for human factor VIII inhibitor antibodies by immunoblotting and antibody neutralization, Blood 74 (1989) 1618-1626.
[7] P. Lollar, Analysis of factor VIII inhibitors using hybrid human/porcine factor VIII, Thromb Haemost 78 (1997) 647-651.
[8] J. F. Healey, I. M. Lubin, H. Nakai, E. L. Saenko, L. W. Hoyer, D. Scandella, P. Lollar, Residues 484-508 contain a major determinant of the inhibitory epitope in the A2 domain of human factor VIII, J Biol Chem 270 (1995) 14505-14509.
[9] I. M. Lubin, J. F. Healey, R. T. Barrow, D. Scandella, P. Lollar, Analysis of the human factor VIII A2 inhibitor epitope by alanine scanning mutagenesis, J Biol Chem 272 (1997) 30191-30195.
[10] P. J. Fay, D. Scandella, Human inhibitor antibodies specific for the factor VIII A2 domain disrupt the interaction between the subunit and factor IXa, J Biol Chem 274 (1999) 29826-29830.
[11] D. Zhong, E. L. Saenko, M. Shima, M. Felch, D. Scandella, Some human inhibitor antibodies interfere with factor VIII binding to factor IX, Blood 92 (1998) 136-142.
[12] J. F. Healey, R. T. Barrow, H. M. Tamim, I. M. Lubin, M. Shima, D. Scandella, P. Lollar, Residues Glu2181-Val2243 contain a major determinant of the inhibitory epitope in the C2 domain of human factor VIII, Blood 92 (1998) 3701-3709.
[13] D. Scandella, G. E. Gilbert, M. Shima, H. Nakai, C. Eagleson, M. Felch, R. Prescott, K. J. Rajalakshmi, L. W. Hoyer, E. Saenko, Some factor VIII inhibitor antibodies recognize a common epitope corresponding to C2 domain amino acids 2248 through 2312, which overlap a phospholipid-binding site, Blood 86 (1995) 1811-1819.
[14] M. T. Reding, D. K. Okita, B. M. Diethelm-Okita, T. A. Anderson, B. M. Conti-Fine, Human CD4+ T-cell epitope repertoire on the C2 domain of coagulation factor VIII, J Thromb Haemost 1 (2003) 1777-1784.
[15] K. P. Pratt, J. Qian, E. Ellaban, D. K. Okita, B. M. Diethelm-Okita, B. Conti-Fine, D. W. Scott, Immunodominant T-cell epitopes in the factor VIII C2 domain are located within an inhibitory antibody binding site, Thromb Haemost 92 (2004) 522-528.
[16] K. Sou, T. Endo, S. Takeoka, E. Tsuchida, Poly(ethylene glycol)-modification of the phospholipid vesicles by using the spontaneous incorporation of poly(ethylene glycol)-lipid into the vesicles, Bioconjug Chem 11 (2000) 372-379.
[17] G. R. Bartlett, Phosphorus assay in column chromatography, J Biol Chem 234 (1959) 466-468.
[18] V. S. Purohit, K. Ramani, R. S. Kashi, M. J. Durrani, T. J. Kreiger, S. V. Balasubramanian, Topology of factor VIII bound to phosphatidylserine-containing model membranes, Biochim Biophys Acta 1617 (2003) 31-38.

[19] T. D. Heath, B. A. Macher, D. Papahadjopoulos, Covalent attachment of immunoglobulins to liposomes via glycosphingolipids, Biochim Biophys Acta 640 (1981) 66-81.

[20] J. Over, Methodology of the one-stage assay of Factor VIII (VIII:C), Scand J Haematol Suppl 41 (1984) 13-24.

[21] S. Stoilova-McPhie, B. O. Villoutreix, K. Mertens, G. Kemball-Cook, A. Holzenburg, 3-Dimensional structure of membrane-bound coagulation factor VIII: modeling of the factor VIII heterodimer within a 3-dimensional density map derived by electron crystallography, Blood 99 (2002) 1215-1223.

[22] L. Bi, A. M. Lawler, S. E. Antonarakis, K. A. High, J. D. Gearhart, H. H. Kazazian, Jr., Targeted disruption of the mouse factor VIII gene produces a model of haemophilia A, Nat Genet. 10 (1995) 119-121.

[23] J. Qian, M. Borovok, L. Bi, H. H. Kazazian, Jr., L. W. Hoyer, Inhibitor antibody development and T cell response to human factor VIII in murine hemophilia A, Thromb Haemost 81 (1999) 240-244.

[24] B. Verbruggen, I. Novakova, H. Wessels, J. Boezeman, M. van den Berg, E. Mauser-Bunschoten, The Nijmegen modification of the Bethesda assay for factor VIII:C inhibitors: improved specificity and reliability, Thromb Haemost 73 (1995) 247-251.

[25] J. R. Lakowicz, Principles of fluorescence spectroscopy, Kluwer Academic/Plenum,

The invention claimed is:

1. A pharmaceutical composition comprising lipidic structures, wherein the lipidic structures comprise:
   a. phosphatidylethanolamine (PE) derivatized with polyethylene glycol (PEG) (PEG-derivatized PE);
   b. an amphipathic lipid selected from the group consisting of phosphatidylcholine (PC), phosphatidylglycerol (PG), and combinations thereof, and, optionally, PE;
   c. a negatively charged lipid selected from the group consisting of phosphatidylserine (PS), phosphatidic acid (PA) and combinations thereof; and
   d. Factor VIII,
   wherein the ratio of amphipathic lipid to the negatively charged lipid is between 50:50 to 90:10 and the amount of PEG derivatized PE is from 1-15 mole %, and
   wherein the immunogenicity of Factor VIII is reduced over the immunogenicity of free Factor VIII.

2. The pharmaceutical composition of claim 1, wherein the lipidic structure is selected from the group consisting of liposomes, micelles, cochleates, and combinations thereof.

3. The pharmaceutical composition of claim 1, wherein the amphipathic lipid is PC and the negatively charged lipid is PS.

4. The pharmaceutical composition of claim 2, wherein the ratio of PC to PS is 70:30.

5. The pharmaceutical composition of claim 1, wherein the amphipathic lipid is PC and PE and the negatively charged lipid is PS and the ratio of PC:PS:PE is 80:10:10 or 70:10:20.

6. The pharmaceutical composition of claim 2, wherein the ratio of PC:PS:PEG-derivatized PE is 70:30:15.

7. The pharmaceutical composition of claim 1, wherein the liposomes further comprise PE that is not derivatized with PEG in the amount of 1-10 mole %.

8. The pharmaceutical composition of claim 1, wherein the two acyl chains of the phospholipids have between 12-22 carbon atoms in each chain, wherein the two acyl chains have the same or different number of carbon atoms.

9. The pharmaceutical composition of claim 7, wherein the acyl chain is selected from the group consisting of myristic acid, palmitic acid, stearic acid.

10. The pharmaceutical composition of claim 1, further comprising 0.5-30 mole % cholesterol.

11. The pharmaceutical composition of claim 1 wherein there is a spacer of 6-12 carbon atoms between the PE and the PEG moieties of the PEG derivatized PE.

12. A method of making the pharmaceutical composition of claim 1, comprising:
   a. preparing liposomes comprising PC, PS and activated PE;
   b. adding Factor VIII; and
   c. adding activated PEG such that the activated PEG binds to the activated PE.

13. The method of claim 12, wherein a spacer arm comprising 6-12 carbon atoms is attached to either PEG or PE.

* * * * *